United States Patent [19]
Ahr et al.

[11] Patent Number: 5,643,241
[45] Date of Patent: *Jul. 1, 1997

[54] DISPOSABLE ABSORBENT ARTICLE HAVING A PUMP AND AN INFLATABLE COMPONENT

[75] Inventors: Nicholas Albert Ahr, Cincinnati; Donald Carroll Roe, West Chester, both of Ohio

[73] Assignee: The Procter & Gamble Company, Cincinnati, Ohio

[*] Notice: The term of this patent shall not extend beyond the expiration date of Pat. No. 5,582,604.

[21] Appl. No.: 441,154

[22] Filed: May 15, 1995

Related U.S. Application Data

[63] Continuation of Ser. No. 250,892, May 31, 1994, Pat. No. 5,582,604.

[51] Int. Cl.⁶ .............................. A61F 13/15; A61F 13/20
[52] U.S. Cl. ........................................ 604/385.1; 604/358
[58] Field of Search ..................................... 604/358, 373, 604/378, 367, 369, 385.1; 2/111, DIG. 3

[56] References Cited

U.S. PATENT DOCUMENTS

| | | |
|---|---|---|
| 19,418 | 2/1858 | Hall . |
| 1,112,186 | 9/1914 | Andersen . |
| 2,582,648 | 1/1952 | Mowbray . |
| 2,597,924 | 5/1952 | Davenport et al. . |
| 3,512,528 | 5/1970 | Whitehead et al. . |
| 3,626,944 | 12/1971 | Schaar . |
| 3,881,491 | 5/1975 | Whyte . |
| 3,921,232 | 11/1975 | Whyte . |
| 4,224,746 | 9/1980 | Kim . |
| 4,245,406 | 1/1981 | Landay et al. . |
| 4,263,728 | 4/1981 | Frecentese . |
| 4,397,104 | 8/1983 | Doak . |
| 4,462,171 | 7/1984 | Whispell . |
| 4,643,727 | 2/1987 | Rosenbaum . |
| 4,676,785 | 6/1987 | Battista . |
| 4,705,050 | 11/1987 | Markham . |
| 4,723,953 | 2/1988 | Rosenbaum et al. . |
| 4,763,426 | 8/1988 | Polus et al. . |
| 4,790,839 | 12/1988 | Ahr . |
| 4,964,858 | 10/1990 | Livny . |
| 5,040,525 | 8/1991 | Georgijevic . |
| 5,113,599 | 5/1992 | Cohen et al. . |
| 5,158,767 | 10/1992 | Cohen et al. . |
| 5,171,236 | 12/1992 | Dreier et al. . |
| 5,176,672 | 1/1993 | Bruemmer et al. . |
| 5,222,312 | 6/1993 | Doyle . |
| 5,253,435 | 10/1993 | Auger et al. . |
| 5,257,470 | 11/1993 | Auger et al. . |
| 5,306,266 | 4/1994 | Freeland . |
| 5,330,459 | 7/1994 | Lavon et al. . |

FOREIGN PATENT DOCUMENTS

| | | |
|---|---|---|
| 0340320A1 | 11/1989 | European Pat. Off. . |
| 0486006A2 | 5/1992 | European Pat. Off. . |
| 2561078 | 9/1985 | France . |
| 3517192A1 | 11/1986 | Germany . |

OTHER PUBLICATIONS

Plitek Article Dated 1990; Plitek Thin Film Valve Advertisement Copyrighted 1990.

*Primary Examiner*—P. Zuttarelli
*Attorney, Agent, or Firm*—Gerry S. Gressel; Larry L. Huston; E. Kelly Linman

[57] ABSTRACT

A diaper having an inflatable component and a pump is disclosed. The pump has a pump chamber having an inlet port and an outlet port, and a resilient chamber wall. The resilient chamber wall is deformable to displace air from the pump chamber to the inflatable component. A check valve provides unidirectional flow from the pump to the inflatable component.

7 Claims, 3 Drawing Sheets

DISPOSABLE ABSORBENT ARTICLE HAVING A PUMP AND AN INFLATABLE COMPONENT

This is a continuation of application Ser. No. 08/250,892 filed May 31, 1994; now U.S. Pat. No. 5,582,604.

FIELD OF THE INVENTION

The present invention is related to disposable absorbent articles having an inflatable component, such as a spacer for maintaining a void space for receiving fecal matter, and a pump for inflating the inflatable component.

BACKGROUND OF THE INVENTION

Disposable absorbent articles are used to absorb and retain body exudates, such as urine, fecal material, menses, and the like. A particular desired feature of disposable absorbent articles is the capability to acquire and hold body exudates to minimize leakage of body exudates from between the absorbent article and the wearer.

References in the art teach adding a spacer to the disposable absorbent article for aiding in the containment of fecal material. Such spacers suffer from the disadvantage that they increase the thickness of the disposable absorbent article, and thereby increase shipping and storage costs. Such spacers may also be perceived by consumers to be uncomfortable because of their thickness prior to application of the diaper to the wearer. Examples of such references include U.S. Pat. No. 5,176,672 issued Jan. 5, 1993 to Bruemmer et al., U.S. Pat. No. 5,171,236 issued Dec. 15, 1992 to Dreier et al., and U.S. patent application Ser. No. 07/898,047, Spacers for Use in Disposable Absorbent Articles and Disposable Absorbent Articles Having Such Spacers, filed Jun. 11, 1992 by Allen et al.

Still other references disclose absorbent articles having inflatable structures. French Patent Application 2,561,078 published Sep. 20, 1985 in the name of Lefebvre discloses a diaper having a structure which is inflatable by mouth. Such inflation can be awkward or inconvenient, especially in public areas or when the diaper is already fastened to the wearer. Such an arrangement is also disadvantageous because of sanitary considerations.

U.S. Pat. Nos. 3,881,491 and 3,921,232 issued to Whyte on May 6, 1975 and Nov. 25, 1975 respectively, disclose disposable absorbent articles having self inflating structures. The self inflating structures include a wall of semipermeable material through which body fluids can pass, and a gas evolving material which interacts with an activator material (e.g., urine) to inflate the structure. The structure taught by Whyte primarily prevents core densification and suffers from the disadvantage that it requires an activator material from an external source, such as urine. The wearer may not urinate at the desired time, in the desired location, or in the desired amount to properly inflate the structure. U.S. patent application Ser. No. 08/081,733 filed Jun. 23, 1993 in the name of Ahr et al. and Ser. No. 08/081,536 filed Jun. 23, 1993 in the name of LaVon et al. disclose inflatable diaper components whose inflation requires wetting of the component or mixture of two different materials.

Accordingly, it is an object of the present invention to provide a disposable absorbent article having a component that is inflatable at the point of use of the absorbent article by a wearer, or by a person caring for the wearer, before or after the absorbent article is fastened to the wearer.

It is also an object of the present invention to provide a diaper having a component which can be inflated to the degree desired by the user.

It is a further object of the present invention to provide an absorbent article having an inflatable component and a pump disposed on the disposable absorbent article for inflating the inflatable component.

SUMMARY OF THE INVENTION

The invention comprises a disposable absorbent article having a topsheet, a backsheet, an absorbent core disposed intermediate the topsheet and backsheet, an inflatable component, and a pump disposed on the absorbent article for inflating the inflatable component. The pump can be disposed intermediate the topsheet and the backsheet. In one embodiment the pump is joined to the backsheet. The pump can comprise a pump chamber having an inlet port and an outlet port, and a resilient chamber wall. The resilient chamber wall is deformable to displace air from the pump chamber through the outlet port and into the inflatable component. The inlet port of the pump chamber can be positioned outward of the perimeter of the absorbent core and be positioned subjacent a portion of the topsheet for receiving air through the topsheet.

In another embodiment, the pump can include a resilient, porous element, such as open celled foam. The disposable absorbent article can further include a check valve disposed downstream of the outlet port of the pump chamber for providing unidirectional flow from the pump to the inflatable component.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, training pants and briefs, diaper holders and liners, feminine hygiene garments such as sanitary napkins, and the like.

Figure 1:
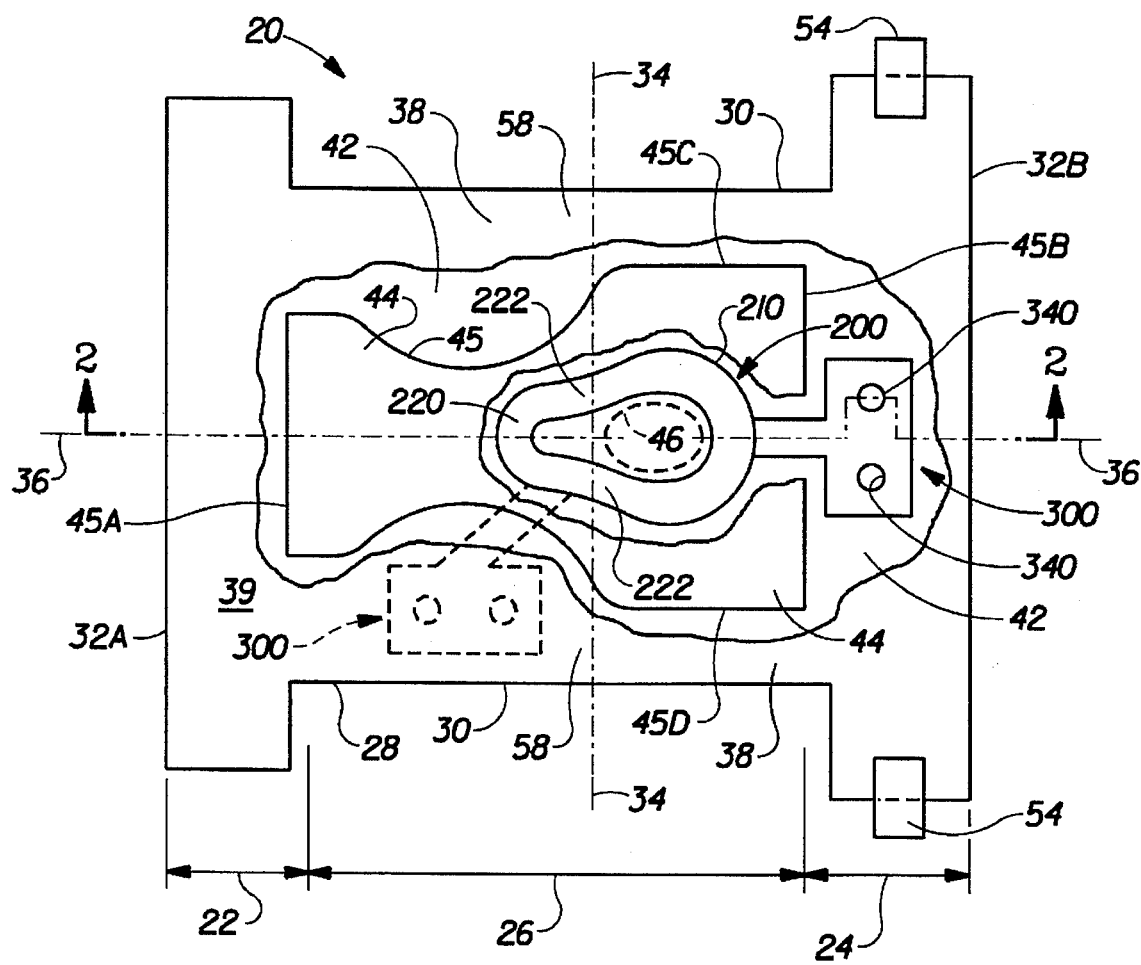
FIG. 1 is a top plan view of a disposable diaper with portions of the topsheet and absorbent core shown cutaway to illustrate an inflatable keyhole shaped spacer and a pump for inflating the spacer.

FIG. 1 is a plan view of the diaper 20 of the present invention in its flat-out, uncontracted state (i.e, with elastic induced contraction pulled out) with portions of the structure being cutaway to more clearly show the construction of the diaper 20 and with the portion of the diaper 20 which faces or contacts the wearer, the inner surface, oriented towards the viewer. The diaper 20 is shown in FIG. 1 to have a front waist region 22, a rear waist region 24, a crotch region 26, and a periphery 28 comprising longitudinal edges 30 and front and rear lateral end edges 32A and 32B. The diaper 20 also has a lateral centerline 34 and a longitudinal centerline 36.

As used herein, the "longitudinal" dimension, direction, or axis of the diaper 20 is aligned front to back with respect to the wearer as the disposable absorbent article is worn. The "lateral" or "transverse" dimension, direction, or axis of the diaper 20 is orthogonal the longitudinal direction and is sideways aligned as the diaper 20 is worn. The "Z-direction" is orthogonal to both the longitudinal and transverse directions, and is illustrated in FIG. 2.

The front waist region 22 and the rear waist region 24 are those portions of the diaper 20 which, when worn, encircle the waist of the wearer and are generally the highest elevation of the diaper 20 when the wearer is in the standing position. The crotch region 26 is disposed between the front and rear waist regions 22, 24 and is that part of the diaper 20 which, when worn, is between the wearer's legs.

Figure 2:
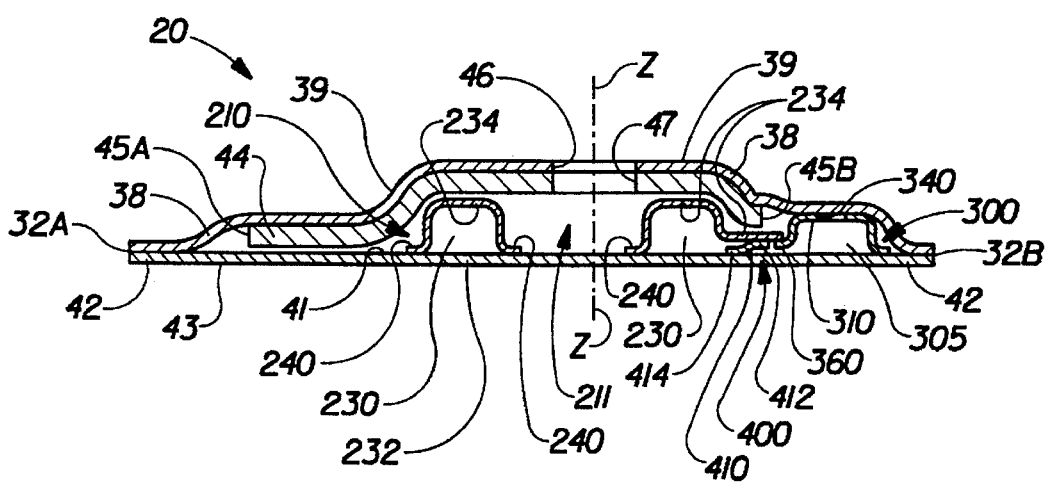
FIG. 2 is an sectional view taken along line 2—2 in FIG. 1 showing the spacer, the pump, and a check valve.

As shown in FIGS. 1 and 2, the diaper 20 comprises a liquid pervious topsheet 38, a liquid impervious backsheet 42 joined with the topsheet 38, and an absorbent core 44 disposed intermediate the topsheet 38 and the backsheet 42. The absorbent core 44 can comprise one or more layers, with one layer shown in the Figures. The absorbent core 44 has a perimeter 45 which includes front and rear laterally extending ends 45A and 45B, as well as side edges 45C and 45D. The absorbent core 44 does not extend longitudinally into the front and rear waist regions 22, 24, but terminates in the crotch region 26 at front and rear laterally extending ends 45A and 45B. The diaper 20 has side margins 58 extending laterally from the absorbent core side edges 45C and 45D to the longitudinal edges 30 of the diaper 20. The side margins 58 include those portions of the topsheet 38 and backsheet 42 which extend laterally outward from the absorbent core side edges 45C and 45D.

The diaper 20 has an inner surface 39 comprising that portion of the diaper 20 which is positioned adjacent to the wearer's body during use (i.e., the inner surface 39 generally is formed by at least a portion of the topsheet 38. The diaper also has an outer surface 43 comprising that portion of the diaper 20 which is positioned way from the wearer's body (i.e., the outer surface 43 generally is formed by at least a portion of the backsheet 42 and other components joined to the backsheet 42.)

The diaper 20 according to the present invention also comprises at least one inflatable component 200, and a pump 300 for inflating the inflatable component at the point of use of the disposable article. The inflatable component 200 is inflatable from a first thickness T1 (FIG. 3) to have a predetermined shape having a second thickness T2 (FIG. 4) substantially greater than the first thickness T1. The inflatable component 200 can comprise a spacer 210 disposed intermediate the topsheet 38 and the backsheet 42 for maintaining a Z-direction fecal void space 211, as shown in FIG. 2.

The pump 300 can be disposed intermediate the topsheet 38 and the backsheet 42. The pump 300 can comprise a pump chamber 305 having at least one inlet port 340 and at least one outlet port 360. The pump 300 can also comprise a resilient chamber wall 310. The resilient chamber wall 310 forms at least a portion of the boundary of the pump chamber 305. The resilient chamber wall 310 is deformable, such as by a finger tip, to displace a gas such as air from the pump chamber 305 through the outlet port 360 and into the spacer 210. By "resilient chamber wall" it is meant that the chamber wall 310 can be repeatedly deformed, such as by a force exerted by a finger tip, and that upon release of the deforming force the chamber wall 310 resumes its undeformed shape, and thereby causes air to he drawn into the pump chamber 310 through the inlet port 340. A check valve 400 can be disposed downstream of the outlet port 360 to provide unidirectional flow from the pump 300 to the inflatable spacer 210.

Referring to the components of the diaper 20 shown in FIG. 1 in more detail, the diaper 20 preferably also includes a pair of fasteners 54, such as tape tabs or mechanical fasteners, positioned in the rear waist region 24 for fastening the diaper 20 to the wearer. The diaper can also have gasket cuffs (not shown), barrier leg cuffs (not shown), and i waist elastic feature, such as an elasticized waist band (not shown). U.S. Pat. No. 3,848,594 issued Nov. 19, 1974 to Buell and Reissue U.S. Pat. No. B1 4,662,875 reissued May 5, 1987 to Hirotsu et al. are incorporated herein by reference to illustrate suitable tape tab fasteners 54. U.S. Pat. No. 3,860,003 issued Jan. 14, 1975 to Buell; U.S. Pat. No. 4,081,301 issued Mar. 28, 1978 to Buell; U.S. Pat. No. 4,695,278 issued Sep. 22, 1987 to Lawson; and U.S. Pat. No. 4,938,755 issued Jul. 3, 1990 to Foreman are incorporated herein by reference to illustrate gasket cuffs and barrier leg cuffs. U.S. Pat. No. 4,515,595 issued May 17, 1985 to Kievit; and U.S. Pat. No. 4,816,025 issued Mar. 28, 1989 to Foreman are incorporated herein by reference to illustrate an elasticized waistband for a diaper 20.

FIG. 1 shows an embodiment of the diaper 20 in which the topsheet 38 and the backsheet 42 have length and width dimensions generally larger than those of the absorbent core 44. The topsheet 38 and the backsheet 42 extend longitudinally beyond the laterally extending core ends 45A and 458 to form the front and rear waist regions 22 and 24. The topsheet 38 and backsheet 42 extend laterally beyond core side edges 45C and 45D to form side margins 58. While the topsheet 38, the backsheet 42, and the absorbent core 44 may be assembled in a variety of well known configurations, preferred diaper configurations are described generally in U.S. Pat. No. 3,860,003 issued to Buell on Jan. 14, 1975 and U.S. Pat. No. 5,151,092 issued to Buell on Sep. 29, 1992, each of which is incorporated herein by reference.

The spacer 210 is preferably inflatable from the first thickness T1 to the second, substantially greater thickness T2. By "substantially greater" it is meant that T2 is at least 10 times, and preferably at least about 50 times as great as T1. The spacer 210 should have a second thickness T2 (FIG. 7) in the Z-direction of at least 0.64 centimeters (0.25 inch).

The thicknesses T1 and T2 are measured under a Z-direction compressive loading of 1.0 pound per square inch, where the compressive loading is applied over an area having a circular area of application, or footprint, of about 6.45 square centimeters (1.0 square inch).

The spacer 210 illustrated in FIG. 1 has a generally "keyhole" shape comprising a closed figure. Other suitable closed shapes for the spacer 210 include, but are not limited to, circles, squares, and elongated shapes, such as ovals and rectangles. Alternatively, the spacer 210 can comprise a generally U-shaped figure opening rearward or forward. The spacer 210 preferably includes a laterally extending portion 220 joining two longitudinally extending portions 222. Suitable shapes and dimensions for a spacer 210 are disclosed in U.S. patent application Ser. No. 08/081,733, filed Jun. 23, 1993 in the name of Ahr et at., which applications is incorporated herein by reference.

In embodiments where the inflated component 200 comprises a fecal void volume spacer 210, the topsheet 38 and the absorbent core 44 can comprise apertures 46 and 47 respectively (the aperture 46 is shown in phantom in FIG. 1). The apertures 46 and 47 are registered with one another to provide a passageway for the communication of fecal material from the wearer's anal opening into the void space 211. Alternatively, the apertures 46 and 47 can be omitted, and the spacer 210 can provide a depression on the surface of the topsheet for holding fecal matter away from the wearer's skin.

As used herein, a "void space" is a cavity intermediate the topsheet 38 and the backsheet 42, which cavity is sized to accept fecal material. The void space 211 can be closed if the absorbent core 44 is compressed between the topsheet 38 and the backsheet 42 by the wearer's weight. When inflated to the have the second thickness T2, the spacer 210 supports the wearer's weight and thereby maintains the void space 211 such that the void space 211 has a thickness of at least about 0.65 centimeters (0.25 inch) and a volume of at least about 16.4 cubic centimeters (1.0 cubic inches).

The topsheet 38 and backsheet 42 are generally coextensive and at least partially peripherally joined together. As used herein the term "joined" refers to the condition where a first member or component is affixed or connected to a second member or component, either directly, or indirectly where the first member or component is affixed or connected to an intermediate member or component which in turn is affixed or connected to the second member or component.

The topsheet 38 and backsheet 42 may be joined by any means well known in the art, such as adhesive bonding or heat sealing. A particularly preferred method of joining the topsheet 38 and backsheet 42 is using hot-melt adhesive such as manufactured by Century Adhesives, Inc. of Columbus, Ohio and marketed as Century 5227 or HL1258 adhesive sold by the H. B. Fuller Company of St. Paul, Minn. In a particularly preferred embodiment, adhesive joining is accomplished by longitudinally oriented adhesive bands or spirals.

As used herein, the term "absorbent core" refers to any component of the diaper 20 used for absorbing and retaining body exudates. The absorbent core 44 may have opposed major faces and may, if desired, be encased by one or more layers of tissue (not shown). The absorbent core 44 may be made from a variety of commonly used materials such as comminuted wood pulp, typically referred to as airfelt. If desired, the absorbent core 44 may further contain absorbent gelling materials as is commonly used in the art. In particular, the absorbent core 44 may be made in accordance with the teachings of U.S. Pat. No. 4,610,678 issued Sep. 9, 1986 to Weisman et al.; U.S. Pat. No. 4,834,735 issued May 30, 1989 to Alemany et al.; U.S. Pat. No. 5,217,445 issued Jun. 8, 1993 to Cook et al.; and U.S. Pat. No. 5,234,423 issued Aug. 10, 1993 to Alemany et al., which patents are incorporated herein by reference for the purpose of showing how to make an absorbent core 44 suitable for use with the present invention. Absorbent gelling materials made in accordance with commonly assigned U.S. Pat. No. Re 32,649 issued Apr. 19, 1988 to Brandt et al. are suitable for use in a diaper 20 according to the present invention.

The core 44 can be joined to the underside of the topsheet 38, as shown in FIG. 2. Alternatively, the core 44 can be joined to the backsheet 42, or the core 44 can comprise two or more layers. The absorbent core 44 may be adhesively joined to the topsheet 38 or backsheet 42 by any attachment means well known in the art. Particularly preferred attachment means are adhesive spirals and longitudinal and transverse bands of adhesive. Particularly preferred types of adhesive are manufactured by Century Adhesives, Inc. of Columbus, Ohio as Century 5227, HL-1258 Adhesive sold by the H. B. Fuller Company of St. Paul, Minn. and XPO-9-035 adhesive manufactured by the Minnesota Mining and Manufacturing Company of St. Paul, Minn.

Referring back to FIG. 1, the "topsheet" refers to any liquid pervious facing of the diaper 20 which contacts the skin of the wearer while the diaper 20 is worn and prevents substantial contact of the absorbent core 44 with the skin of the wearer. The topsheet 38 is preferably compliant, tactilely pleasant and non-irritating to the skin of the wearer. Preferably the topsheet 38 is treated to he hydrophilic, to more readily transport body exudates to the absorbent core 44.

A suitable topsheet 38 may be manufactured from materials such as porous foams, apertured plastic films, natural fibers (e.g., wood fibers or cotton fibers), synthetic fibers (e.g., polyester or polypropylene fibers) or a combination of the foregoing. A particularly preferred topsheet 38 comprises polypropylene fibers having a denier of about 2.2 and a length of about 15.9 millimeters (0.62 inches). The topsheet 38 may he manufactured according to a number of techniques. For example, the topsheet 38 may be a nonwoven web of fibers spunbonded, carded, wet-laid, meltblown, hydroentangled, combinations of the above, or the like. One suitable topsheet 38 is carded and thermally bonded and has a basis weight of about 18 to about 25 grams per square meter. A suitable topsheet 38 is marketed by Veratec, Inc., Division of International Paper Company of Walpole, Mass. under the designation P-8.

The apertures 46 and 47 are preferably laterally centered on the longitudinal axis 36. The aperture 46 may be of any shape desired with a suitable shape being an oval having a longitudinal dimension of about 5.1 centimeters (2.0 inches) and a transverse dimension of about 3.8 centimeters (1.5 inches). The rearwardmost edge of the aperture 46 is disposed at least about 15.2 centimeters (6.0 inches), and preferably about 17.8 centimeters (7.0 inches) to about 21.6 centimeters (8.5 inches) from the rear edge 32B of the diaper 20 while it is worn.

Aperture 47 is registered with aperture 46, and preferably has a shape the same as, or similar to, the shape of aperture 46. Preferably, the spacer 210 is registered with the apertures 46 and 47, such that spacer 210 does not substantially obstruct aperture 46 or aperture 47, and such that at least a portion of each aperture 46 and 47 is disposed intermediate the longitudinally extending portions 222 of spacer 210.

The backsheet 42 is impervious to fluids, such as urine, and prevents fluids absorbed by and contained in the absorbent core 44 from wetting undergarments, clothing and bedding. As used herein the "backsheet" refers to any barrier disposed outwardly of the absorbent core 44 as the diaper 20 is worn and which contains absorbed liquids within the diaper 20. The backsheet 42 is preferably manufactured from a thin thermoplastic film, although other flexible liquid impervious materials may also be used. As used herein, the term "flexible" refers to materials which are compliant and will readily conform to the general shape and contours of the human body.

The backsheet 42 may comprise a woven or nonwoven material, polymeric films such as thermoplastic films of polyethylene or polypropylene, or composite materials such as film-coated nonwoven material. The backsheet 42 can be a thermoplastic film having a thickness of from about 0.01 millimeters to about 0.051 millimeters (0.0005 to 0.002 inches). If desired, the backsheet 42 may be embossed or matte finished to provide a clothlike appearance. A suitable material from which the backsheet 42 can be formed is a polyethylene film having a thickness of from about 0.012 mm to about 0.051 mm. Exemplary polyethylene films are manufactured by Clopay Corp. of Cincinnati, Ohio under the designation P-18-1401, and by Tredegar Corporation of Richmond, Va. under the designations X8297 and HTS-5, FSII.

Referring again to FIG. 1, the spacer 210 can have a keyhole shape comprising a generally closed figure. The keyhole shape shown in FIG. 1 has a reduced lateral width oriented towards the front waist region 22 to comfortably accommodates the thighs of the wearer. Alternatively, the spacer 210 can have a shape comprising an open figure, such as a generally U-shaped configuration that opens rearwardly. A suitable U-shape configuration for the spacer 210 is shown in U.S. Pat. No. 5,171,236 issued Dec. 15, 1992 to Dreier et al., which patent is incorporated herein by reference.

Referring to FIGS. 1 and 2, the spacer 210 comprises one or more inflatable chambers 230. Inflatable chambers 230 can be formed by peripherally joining two chamber walls 232 and 234 at seams 240. In FIGS. 1 and 2 the chamber wall 232 comprises a portion of the backsheet 42, and the chamber wall 234 is joined directly to the surface 41 of the backsheet 42. Alternatively, the chamber wall 232 can comprise a separate wall piece, such as a layer of thermoplastic film disposed intermediate the chamber wall 234 and the backsheet 42.

The walls 232 and 234 of the inflatable chambers 230 should be gas impermeable, and are preferably made from a material which is soft and flexible. In one embodiment, one or both of the walls 232 and 234 can be formed from an elastomeric or stretchable film. The inflatable chamber 230 should maintain an inflated thickness T2 of at least about 0.635 cm (0.25 inch) for at least one hour when the spacer 210 is subjected to a Z-direction compressive load of 1.0 pounds per square inch, and should not completely flatten or rupture when subjected to an impact load such as can result when the wearer sits, or suddenly falls down. Suitable materials for walls 232 and 234 include but are not limited to thermoplastic films, thermoplastic film/metal foil laminates, natural rubbers, and laminated films of natural rubber and synthetic thermoplastics. Suitable materials for walls 232 and 234 include polyethylene films having a thickness between 0.000635 and 0.0127 centimeters (0.25 to 5.0 mils).

Suitable materials from which one or both of the walls 232 and 234 can be made include materials from which the backsheet 42 can be formed, such as the Tredegar X8297 and the Clopay P-18-1401 films listed above. Other suitable materials from which one or both of the walls 232 and 234 can be made include a polyethylene film available from Tredegar Industries designated C-8323.

One or both of the walls 232 and 234 can be pre-formed, such as by vacuum forming or embossing. By way of example, the wall 234 can be vacuum formed to provide a generally semi-circular or rectangular cross-section upon inflation of chamber 230. The walls 232 and 234 can be joined at seams 240 by any suitable joining method such as heat/pressure sealing, adhesive bonding, ultrasonic bonding, or the like. Suitable seams 240 can be formed by heat sealing with a Vertrod Impulse Heat Sealing Unit, Model 12H, 500 watts, set at high pressure with a heat impulse power setting of 1.0 second. Such a heat sealing unit is manufactured by The Vertrod Corporation of Brooklyn, N.Y.

Figure 3:
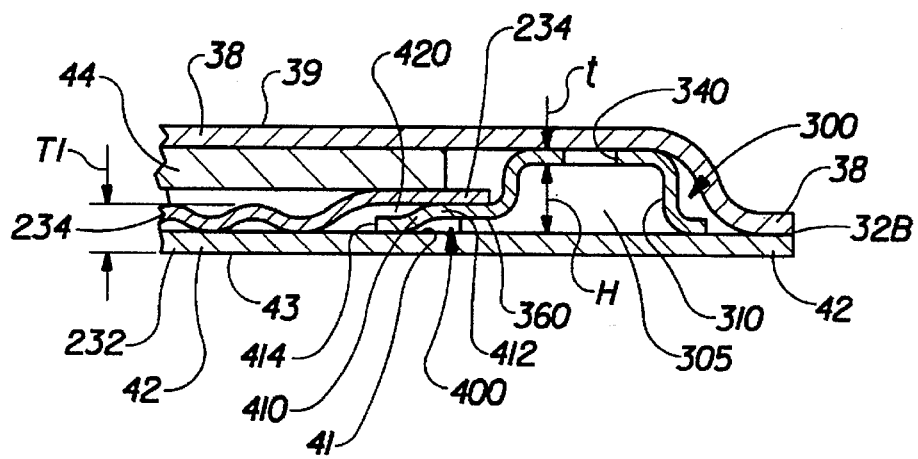
FIG. 3 is an enlarged view of a portion of FIG. 2 showing a deflated spacer, a pump in an undeformed position, and a closed check valve comprising a deformable flap integral with the pump.
Figure 4:
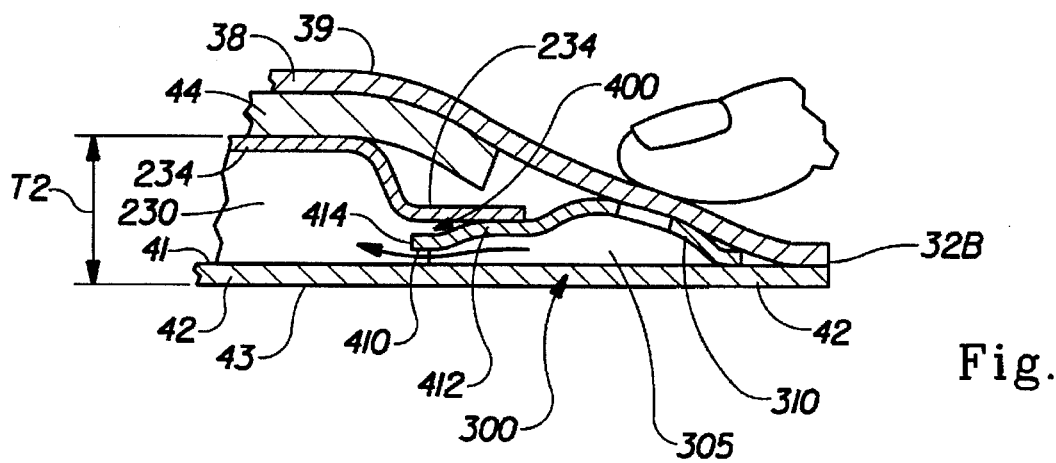
FIG. 4 is an enlarged view of a portion of FIG. 2 showing an inflated spacer, a pump being deformed by a finger tip, and an open check valve.
Figure 5:
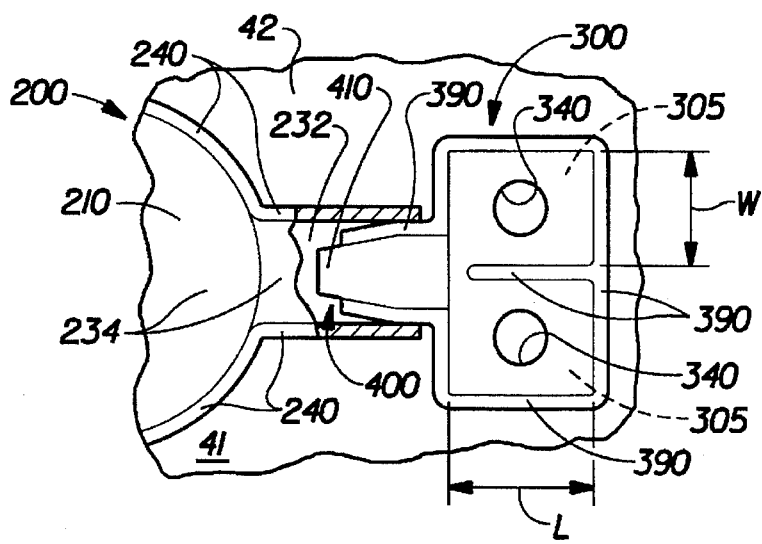
FIG. 5 is a enlarged top plan view of the pump and check valve joined to the backsheet, with a portion of a first wall of a passageway between the spacer and the pump cutaway to show the deformable check valve flap.

Referring to FIGS. 3, 4, and 5, the pump 300 is disposed intermediate the topsheet 38 and the backsheet 42. The pump 300 preferably comprises a pump chamber 305 having at least one inlet port 340 and at least one outlet port 360, and a resilient chamber wall 310 forming a portion of the boundary of the pump chamber 305. The inlet port 340 can extend through the resilient chamber wall 310.

The pump 300 can be directly joined to the backsheet 42 as shown in FIGS. 3–5. In the embodiment shown in FIGS. 3–5 the resilient chamber wall 310 is joined directly to the backsheet 42 so that the pump 300 is integral with the backsheet 42, with the backsheet 42 forming a portion of the boundary of the pump chamber 305. A pump 300 integral with the backsheet 42 is desirable because such an arrangement provides the diaper 20 with a thin, relatively low bulk appearance prior to inflation of the spacer 210. In an alternative embodiment the resilient chamber wall 310 can form the entire boundary of the pump chamber 305, and can be joined to the backsheet 42, either directly or indirectly.

The resilient chamber wall 310 is formed from a material such as rubber or a suitable thermoplastic polymer. A suitable resilient wall 310 can be molded from an Estane 5708 F1 Polyester-Urethane polymer to have a thickness t (FIG. 3) of about 0.3 millimeters. Referring to FIGS. 3 and 5, the pump 300 can have a pair of interconnected pump chambers 305, each having a height H of about 5.0 mm, a length L of about 25.0 mm, and a width W of about 15.0 mm. Each inlet port 340 can have a generally circular shape with a diameter of about 3.0 mm.

The resilient chamber wall 310 can be joined to the backsheet 42 along a seam 390, as shown in FIG. 5. The seam 390 can be formed by any suitable method, including but not limited to heat/pressure sealing, adhesive bonding, or ultrasonic bonding. Suitable seams 390 can be formed with the above described Vertrod Impulse Heat Sealing Unit.

In the embodiment shown in FIGS. 3–5, the topsheet 42 extends longitudinally and laterally outward of the perimeter 45 of the absorbent core 44. The pump 300 has an inlet port 340 disposed outward of the perimeter 45 of the absorbent core. Such an arrangement is desirable so that the relatively thick absorbent core does not interfere with activation of the pump 300. In FIGS. 1, 3, and 4 the pump 300 is shown positioned in the rear waist region 24. Alternatively, the pump 300 can be positioned in the front waist region 22, or in one of the side margins 58, as shown in phantom in FIG. 1.

In FIGS. 1, 3, and 4 the inlet port 340 is disposed subjacent the topsheet 42. As shown in FIG. 4, a finger tip can be placed over the portion of the topsheet 42 overlying the inlet port 340 to restrict air flow from the pump chamber 305 through the inlet port 340. A force applied by the finger tip deforms the resilient chamber wall 360, thereby forcing air from the pump chamber 305 into the chamber 230 of the spacer 210. Upon the release of the pressure applied by the finger tip, the resilient chamber wall 310 regains its undeformed shape, thereby drawing air into the pump chamber 305 through the inlet port 340. The cycle of applying a force by the finger tip can then be repeated to further inflate the spacer 210. The spacer 210 can thereby be inflated to the desired degree by the wearer or diaperer.

Positioning the inlet port 340 subjacent the topsheet 42 and between the core perimeter 45 and the diaper perimeter 28 provides the advantage that the air for filling the pump chamber 305 can pass through the topsheet 38. Such an arrangement permits the entire pump 300 to be discretely concealed between the topsheet 38 and the backsheet, and does not require an air passageway extending from the pump 300 and between the topsheet 38 and backsheet 42 along the perimeter 28 of the diaper 20. In an alternative embodiment, the inlet port 340 can comprise an opening extending between the topsheet 38 and the backsheet 42 along a portion of the perimeter 28. Such an opening between the topsheet and the backsheet is undesirable because it adds to the complexity of manufacturing the diaper 20. In another alternative embodiment the inlet port 340 can be located in the backsheet 42. However, such an arrangement is generally not preferred because the backsheet 42 functions as a liquid impervious barrier. Therefore, it is generally not desirable to have openings in the backsheet 42. In yet another embodiment the pump 300 can be joined to the surface 43 of the backsheet 42.

The check valve 400 provides unidirectional flow from the pump 300 to the chamber 230 of the spacer 210. Referring to FIG. 2, the check valve 400 can comprise a flexible flap 410 deformable from a first closed position to a second open position. The flap 410 is shown in a closed position in FIGS. 2 and 3, and in an open position in FIG. 4. The flap 410 is shown disposed in a passageway 420 (FIG. 3) having first and second opposed walls corresponding to portions of wall 234 and the backsheet 42. The flap 410 has an upstream flap edge 412 joined to the wall 234 and a downstream edge 414 which engages the backsheet 42 when the flap 410 is in the closed position of FIGS. 2 and 3.

A check valve 400 comprising a flap 410 is relatively thin, and provides the diaper 20 with a thin, relatively low bulk appearance. In FIG. 2 the flap 410 is shown as a separate piece of material joined to the wall 234. Such a flap 410 can be made from the same material from which the wall 234 is formed and have a thickness of between about 0.012 mm to about 0.051 mm. The flap 410 can be joined to the wall 234 by any suitable method, such as by heat sealing with the above mentioned Vertrod Impulse Heat Sealing Unit. In an alternative embodiment shown in FIGS. 3–5, the flap 410 can comprise an extension of the resilient chamber wall 310. Such an extension should have a reduced thickness relative to the thickness t so that the flap 410 is sufficiently flexible to be deformed between the closed and opened positions by the difference in air pressure in the chamber 230 and the pump chamber 305.

Figure 6:
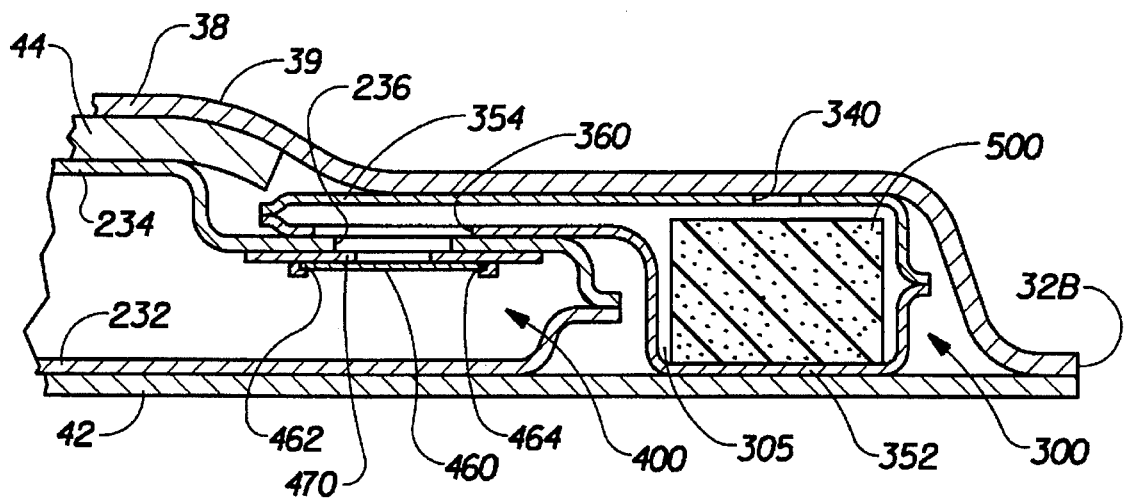
FIG. 6 is a sectional view similar to that of FIG. 3 showing a pump having a resilient element disposed in a pump chamber.
Figure 7:
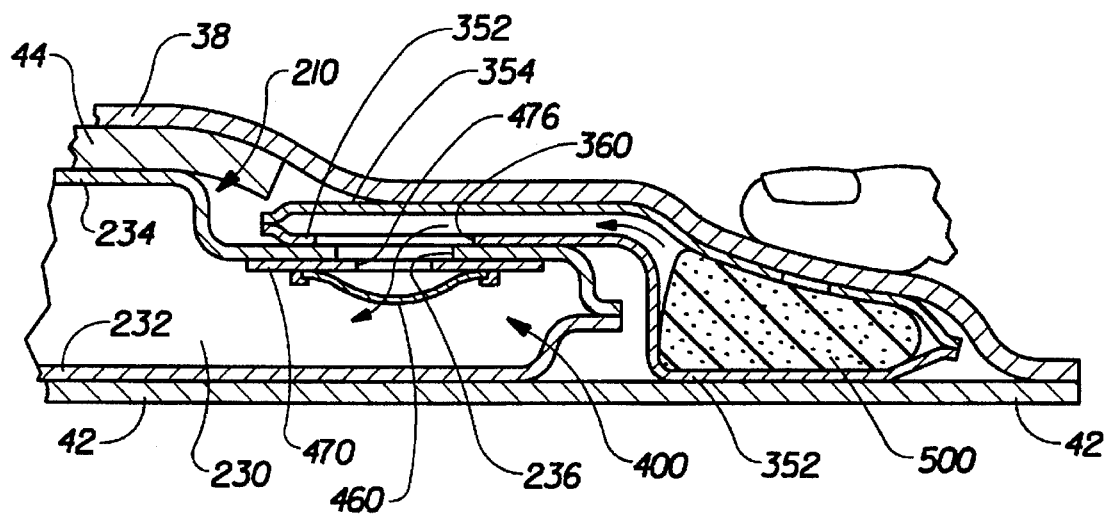
FIG. 7 is a sectional view similar to that of FIG. 6 showing compression of the resilient element to direct air from the pump, through a check valve, and into an inflatable component.

In an alternative embodiment shown in FIGS. 6 and 7, the pump 300 comprises a resilient element 500 disposed within the pump chamber 305. By "resilient element" it is meant an element that can be compressed by a compressive loading from a first thickness to a second thickness less than or equal to about 60 percent of the first thickness, and that the element regains at least about 70 percent of its first thickness within about 15 seconds of release of the compressive loading. The resilient element 500 can be compressed, such as by a finger tip, to force air from the pump chamber 305 into the spacer chamber 230. Upon release of the force compressing the resilient element 500, the resilient element 500 expands, thereby drawing a fresh supply of air into the pump chamber 305 through the inlet port 340.

The resilient element 500 preferably has a relatively low resistance to compressive loading so that the resilient element 500 can be easily compressed with a finger tip, as shown in FIG. 7. Preferably, the resilient element 500 can be compressed from a first thickness to a second thickness less than or equal to about 60 percent of the first thickness by a compressive loading no more than about 1.0 pound per square inch applied with a load application foot having a diameter of about 1.5 inch.

The resilient element 500 should be capable of being cyclically compressed without substantial loss of its unloaded caliper between compression cycles, so that the pump 300 can be activated by repeatedly pressing and releasing the resilient element 500 with a finger tip. Preferably, the resilient element 500 is capable of being cyclically compressed at least 25 times per minute to less than about 60% of its initial, unloaded caliper on each compression cycle, with the resilient element regaining at least about 75% of its initial caliper intermediate each compression cycle.

The compressive loading required to compress the resilient element to less than about 60% of its initial, unloaded caliper during each compression cycle is preferably no more than about 1.0 pound per square inch applied with a load application having a diameter of about 1.5 inch. A suitable testing device for cyclically compressing a resilient element 500 is an EME 599 Advanced Tester manufactured by EME, Inc. of Newbury, Ohio.

In one embodiment the resilient element 500 can be porous so that air drawn into the pump chamber 305 is drawn into the resilient element 500, as well as into the space in the chamber 305 not occupied by the resilient element 500. A suitable resilient element 500 can be formed from a sponge or foam material. In one embodiment, the resilient element 500 can comprise an open celled foam. By "open celled" it meant that the individual cells of the foam are for the most part not completely isolated from each other by the material of the cell walls. The resilient element 500 can have a density of between about 0.01 gram per cubic centimeter and about 0.1 gram per cubic centimeter (gm/cc), as measured under a confining pressure of about 0.0125 pound per square inch applied with a load application foot having a diameter of about 1.5 inch.

One suitable open celled foam from which the resilient element 500 can be made is polyurethane foam having a density of between about 0.015 and about 0.025 gm/cc, such is available as #1230 foam from the American Excelsior Corp. of Cincinnati, Ohio. Other suitable materials from which the resilient element 500 can be made include natural sponge materials having a density of between about 0.015 gm/cc and about 0.025 gm/cc, and polyethylene foam having a density of between about 0.020 gm/cc and about 0.030 gm/cc. Another suitable open celled foam is a foam prepared by polymerizing a high internal phase emulsion, such as is described in U.S. Pat. No. 5,147,345 issued Sep. 15, 1992 to Young et al., which patent is incorporated herein by reference.

The resilient element 500 can have a free, unrestrained Z-direction thickness of about 0.7 inch. Prior to use, the resilient element 500 can be compressed to a reduced Z-direction thickness for shipping and storage. For instance, the resilient element 500 can be compressed to a reduced thickness, and the inlet port 340 can be covered with a releasable seal, such as a piece of adhesive backed film or tape. The seal covering the inlet port 340 prevents air from air entering the chamber 305, and thereby prevents expansion of the resilient element 500. At the point of use of the disposable absorbent article, the seal covering the inlet port 340 can be removed, thereby permitting the resilient element 500 to regain its free, unrestrained thickness.

The pump chamber 305 can be bounded by two pump chamber walls 352 and 354, as shown in FIG. 6. In FIG. 6 the wall 352 is separate from the backsheet 42, but in an alternate embodiment, the wall 352 can comprise a portion of the backsheet 42. The walls 352 and 354 should be formed from a gas impermeable material, such as a thermoplastic film. Suitable materials from which the walls 352 and 354 can be formed include the materials listed above with reference to the backsheet 42 and the spacer chamber walls 232 and 234. The walls 352 and 354 can be peripherally joined by any suitable method including heat/pressure sealing, adhesive bonding, ultrasonic bonding, and the like. The wall 352 can include a pump outlet port 360 which is registered with an opening 236 in the spacer chamber wall 234. The walls 234 and 352 can be joined together adjacent the opening 236 and the outlet port 360 by any suitable method such as heat/pressure sealing, adhesive bonding, and the like to prevent leakage of air from between the walls 234 and 352.

FIGS. 6 and 7 show an alternative embodiment of a check valve 400 for providing uni-directional flow from the pump chamber 305 to the spacer chamber 230. The check valve 400 is shown joined to the spacer chamber wall 234 in FIGS. 6 and 7. The check valve 400 includes a deformable flap 460 supported at first and second ends 462 and 464. The check valve 400 also includes a support piece 470 joined to the wall 234 and having an aperture 476 registered with the outlet port 360. When the air pressure in the spacer chamber 230 is greater than the air pressure in the pump chamber 305 (e.g. when the resilient element 500 is expanding within the pump chamber 305), the pressure differential causes the flap 460 to cover the aperture 476, and thereby prevents flow of air from the chamber 230 into the pump chamber 305. When the air pressure in the pump chamber 305 is greater than the air pressure in the spacer chamber 230 (e.g. when the resilient element 500 is compressed by a finger tip), the pressure differential deforms the flap 460 intermediate the first and second ends 462 and 464, as shown in FIG. 7, to permit air to enter the spacer chamber 230 from the pump chamber 305 through the outlet port 360. A thin film valve having a flap supported at first and second ends and suitable for use as a check valve 400 is manufactured by Plitek, Inc. of Elk Grove Village, Ill. under the tradename PLI-VALV.

In the embodiments shown, the inflatable component 200 comprises a spacer 210. However, components 200 inflatable by the pump 300 are not limited to spacers for providing fecal void volume. For instance, the inflatable component 200 can comprise an inflatable component positioned along the waist regions 22, 24 or the side margins 58, for preventing leakage in the waist regions 22, 24 and side margins 58, respectively.

While particular embodiments of the present invention have been illustrated and described, the scope of the present invention is defined by the appended claims.

What is claimed is:

1. A disposable absorbent article comprising:

a liquid impervious backsheet;

a liquid pervious topsheet joined to the backsheet;

an absorbent core disposed intermediate the topsheet and the backsheet;

an inflatable component disposed on the absorbent article and inflatable from a first thickness to a second thickness substantially greater than the first thickness; and a pump disposed on the absorbent article, the pump having an inlet port for receiving air and an outlet port, and the pump being repeatably deformable to displace air through the outlet port and into the inflatable component for inflating the inflatable component.

2. The disposable absorbent article of claim 1 wherein the pump is disposed intermediate the topsheet and the backsheet.

3. The disposable absorbent article of claim 1 wherein the pump is joined directly to the backsheet.

4. The disposable absorbent article of claim 3 wherein the pump is integral with the backsheet.

5. The disposable absorbent article of claim 2 wherein the topsheet extends outward of a perimeter of the absorbent core, and wherein the pump has an inlet port disposed outward of the perimeter of the absorbent core and subjacent a portion of the topsheet.

6. The disposable absorbent article of claim 1 wherein the pump comprises a resilient chamber wall.

7. A disposable absorbent article comprising:

a liquid impervious backsheet a liquid pervious topsheet joined to the backsheet;

an absorbent core disposed intermediate the topsheet and the backsheet;

an inflatable component disposed on the absorbent article; and a pump disposed on the absorbent article, the pump comprising a pump chamber having an inlet port for receiving air, an outlet port, and a resilient chamber wall, wherein the resilient chamber wall is deformable to displace air from the pump chamber through the outlet port and into the inflatable component.

* * * * *